(12) United States Patent
Fauser et al.

(10) Patent No.: US 11,497,516 B2
(45) Date of Patent: Nov. 15, 2022

(54) MEDICAL INSTRUMENT

(71) Applicant: KARL STORZ SE & Co. KG, Tuttlingen (DE)

(72) Inventors: Heiner Fauser, Tuttlingen (DE); Arno Kohli, Tuttlingen (DE); Sven Grüner, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

(21) Appl. No.: 16/935,577

(22) Filed: Jul. 22, 2020

(65) Prior Publication Data

US 2021/0038242 A1 Feb. 11, 2021

(30) Foreign Application Priority Data

Aug. 5, 2019 (DE) ...................... 10 2019 121 088.7

(51) Int. Cl.
*A61B 17/29* (2006.01)
*A61B 17/00* (2006.01)

(52) U.S. Cl.
CPC .... *A61B 17/29* (2013.01); *A61B 2017/00323* (2013.01); *A61B 2017/2902* (2013.01); *A61B 2017/2947* (2013.01)

(58) Field of Classification Search
CPC .......... A61B 17/29; A61B 2017/00323; A61B 2017/2902; A61B 2017/2947
See application file for complete search history.

(56) References Cited

U.S. PATENT DOCUMENTS

| 2006/0020287 A1* | 1/2006 | Lee ........................ A61B 17/29 606/205 |
| 2008/0255421 A1* | 10/2008 | Hegeman ............. A61B 1/0055 600/139 |
| 2013/0218141 A1 | 8/2013 | Hinman et al. |
| 2015/0164524 A1 | 6/2015 | Malkowski et al. |

(Continued)

FOREIGN PATENT DOCUMENTS

WO   2004052171 A2   6/2004

OTHER PUBLICATIONS

Search Report, DE 10 2019 121 088.7, dated Jun. 30, 2020 (8 pp.).
(Continued)

*Primary Examiner* — Brooke Labranche
(74) *Attorney, Agent, or Firm* — Eversheds Sutherland (US) LLP

(57) ABSTRACT

The present application is directed to a medical instrument with a hollow shaft, a handle arranged at the proximal end of the shaft and a tool tip with a tool arranged at the distal end of the shaft, wherein the tool can be actuated via an actuating element mounted in the shaft, the element being in an operative connection with the handle and the tool tip being pivotable relative to the shaft via a joint mechanism, the joint mechanism having pivoting members, wherein inside the hollow shaft at least one guide device is arranged for the steering wires connecting the pivoting members to the drive. In order that the steering wires can be installed easily and without crossing, the at least one guide device is arranged coaxially on the actuating element, and the at least one a guide device is mounted on the actuating element so that it cannot rotate.

11 Claims, 5 Drawing Sheets

(56) References Cited

U.S. PATENT DOCUMENTS

2016/0100851 A1* 4/2016 Van Andel ............. A61B 10/06
606/174
2020/0222666 A1* 7/2020 Chan ...................... A61B 34/35

OTHER PUBLICATIONS

Search Report, EP 20187708.1, dated Nov. 6, 2020 (6 pp.). (In German).

* cited by examiner

MEDICAL INSTRUMENT

TECHNICAL FIELD

The invention relates to a medical instrument with a hollow shaft, a handle arranged at the proximal end of the shaft and a tool tip with a tool arranged at the distal end, wherein the tool can be actuated via an actuating element mounted axially displaceable in the shaft, said element being in an operative connection with the handle on the proximal side and the tool tip being pivotable relative to the longitudinal axis of the shaft via a joint mechanism, the joint mechanism consisting of pivoting members arranged at the distal end of the shaft, which are connected with a proximal-side drive via steering wires running in the longitudinal direction of the shaft in such a way that a movement of the proximal-side drive causes a corresponding relative movement of the distal-side pivoting members and thus a swiveling of the tool tip, wherein inside the hollow shaft between the distal-side pivoting members and the proximal-side drive at least one guide device is arranged for the steering wires connecting the pivoting members to the drive, wherein recesses are formed in the at least one guide device for at least some of the steering wires.

BACKGROUND OF THE INVENTION

Pivoting members with three, four or more external steering wires/steering cables for bendable medical instruments are known in practice for hand-held and/or robotic instruments. For a sensitive control of the distal end of such a medical instrument, many thin steering wires/steering cables have proven to be more advantageous than a few thicker steering wires/steering cables since, among other things, a more even distribution of force can be achieved in all directions of deflection, and, moreover, thinner steering wires/steering cables allow for more space in the interior for electrical cables and the like.

A medical instrument with pivoting members controlled via steering wires/steering cables is known, for example, from US 2013/0218141 A1.

In addition to the advantages mentioned, the use of many thin steering wires/steering cables also has the disadvantage that the assembly is made significantly more difficult because it is very difficult to thread all steering wires/steering cables together through the hollow shaft tube in a crossing-free and sorted manner from the distal direction through the hollow shaft tube.

WO 2004/052171 A2 discloses a generic medical instrument with guide devices for the steering wires arranged in the interior of the shaft. This known design is very complicated to handle and manufacture.

SUMMARY OF THE INVENTION

Based on this, the object of the invention is to design a medical instrument of the type referenced at the outset in such a way that a simple and crossing-free assembly of the steering wires/steering cables is ensured.

The solution to this problem is characterized according to the invention in that the at least one guide device is arranged coaxially on the actuating element and in that the at least one guide device is mounted on the actuating element such that it cannot rotate.

By using a guide device for the steering wires arranged between the distal-side pivoting members and the proximal-side drive inside the hollow shaft tube, it is possible to bridge the area between the distal-side pivoting members and the proximal-side drive so that the a crossing-free insertion of the guide wires from the distal to the proximal direction is ensured. The guide device inside the shaft may alternatively be arranged on the inside of the hollow shaft tube or as a device that can be inserted into the shaft tube.

The arrangement of the at least one guide device for the steering wires coaxially on the actuating element running centrally in the shaft tube enables a simple pre-assembly of the actuating element to be inserted distally into the hollow shaft tube with the steering wires arranged in a crossing-free manner over the at least one guide device.

The inability of the guide device to rotate is intended to ensure that the steering wires arranged in the at least one guide device cannot rotate helically around the central actuating element.

According to the invention, one or more mutually corresponding non-circular contact surfaces are formed on the guide device and on the actuating element in order to prevent a rotation.

Furthermore, it is proposed, according to the invention, that the at least one guide device comprises at least one rinsing opening in addition to the recesses for the steering wires. The at least one rinsing opening in the guide device is intended to ensure that when the shaft tube is rinsed, the guide devices arranged inside the shaft tube are also rinsed and can therefore be cleaned well.

According to a practical embodiment for forming the guide device, it is proposed, according to the invention, that the at least one guide device is designed as a disk-shaped ring that is arranged transversely to the longitudinal axis of the shaft. The annular disk design is easy to manufacture and provides a stable embodiment of the guide device.

In order to ensure the orderly and crossing-free placement of the steering wires, particularly when the shaft is long, a practical embodiment of the invention proposes that at least two guide devices are arranged on the actuating element at a distance from one another. The use of two or more guide devices further simplifies the assembly since the risk of the steering wires crossing is reduced with each additional guide device.

To form the recesses for the steering wires, it is proposed according to a first embodiment of the invention that the recesses for the steering wires formed in the at least one guide device are designed as through holes. Designing the recesses as through holes has the advantage that once the steering wires have been threaded in, they are permanently guided in a secure manner.

According to an alternative embodiment for the formation of the recesses for the steering wires, the invention proposes that the recesses for the steering wires formed in the at least one guide device are designed as radial inwardly open slots which are open toward the outside. If the recesses are designed as slots open to the outside, each steering wire can be inserted quickly and easily into the associated recess of the guide device.

According to a first practical embodiment using the design of the disk-shaped guide device, it is proposed that the guide device designed as a disk-shaped ring comprises at least one partial area with the recesses for the steering wires and at least one partial area with a rinsing opening.

According to an alternative second embodiment, it is proposed, according to the invention, that the guide device designed as a disk-shaped ring comprises two partial areas with the recesses for the steering wires and two partial areas with rinsing openings with the respective partial areas being arranged offset to one another.

Finally, it is proposed with the invention that when using at least two guide devices arranged on the actuating element and designed as a disk-shaped ring, two guide devices arranged one behind the other in the direction of the longitudinal axis of the shaft are each arranged in such a way that the partial areas provided with the recesses for the steering wires and the partial areas provided with the rinsing openings are arranged offset to one another. The offset arrangement of the partial areas provided with the recesses and the partial areas provided with the rinsing openings ensures that, on the one hand, all the steering wires are guided through the partial areas of the guiding devices arranged one behind the other in a crossing-free manner and, on the other hand, a rinsing liquid flowing through the rinsing openings is deflected several times, thus guaranteeing a complete rinsing of the hollow shaft tube.

BRIEF DESCRIPTION OF THE DRAWINGS

Further features and advantages of the invention can be obtained from the associated drawings in which various exemplary embodiments of a medical instrument, according to the invention, are only shown by way of example without limiting the invention to these exemplary embodiments. The drawings show the following.

DETAILED DESCRIPTION

Figure 1:
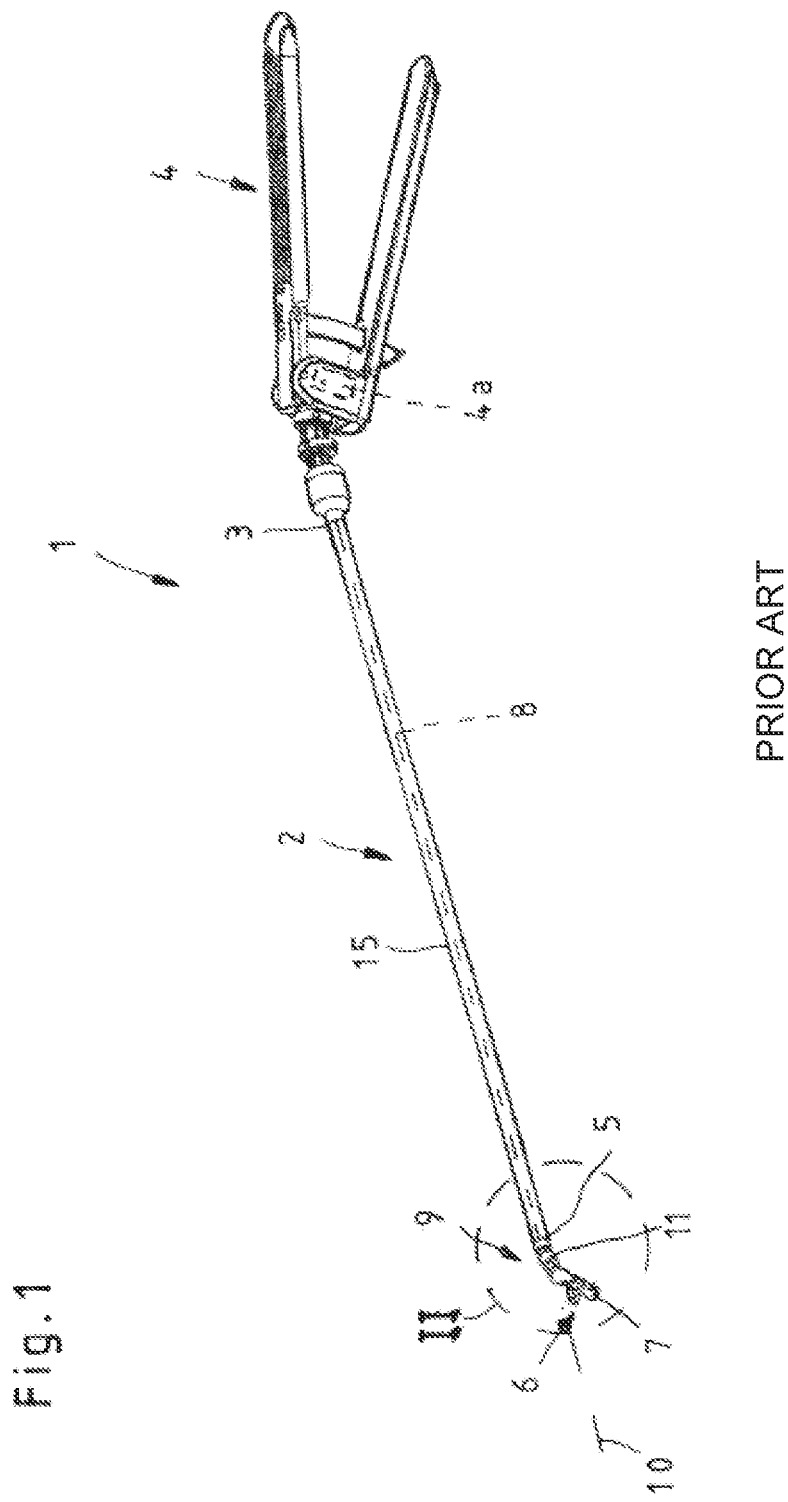
FIG. 1 shows a side perspective view of a medical instrument according to the prior art.

FIG. 1 shows a medical instrument 1 with a hollow shaft 2, a handle 4 arranged at the proximal end 3 of the shaft 2 and a tool tip 6 with a tool 7 arranged at the distal end 5 of the shaft 2, the tool 7 being able to be actuated via an actuating element 8 mounted axially displaceable in the shaft 2, with the actuating element being in an operative connection with the handle 4 on the proximal side.

The tool tip 6 can be pivoted relative to the longitudinal axis 10 of the shaft 2 by means of a joint mechanism 9, the joint mechanism 9 consisting of pivoting members 11 arranged at the distal end of the shaft 5 and having guide wires 12 running in the longitudinal direction of the shaft 2 (FIGS. 2-4) to a proximal-side drive 4a such that a movement of the proximal-side drive 4a causes a corresponding relative movement of the distal-side pivoting members 11 and thus a pivoting of the tool tip 6.

Even if only the term steering wires 12 is used above and below, steering cables may also be used with respect to function, which is why the term steering wires 12 used is to be read and understood synonymously as a steering cable.

The axially displaceable actuating element 8 mounted in the shaft 2 for actuating the tool 7, for example consisting of two jaw parts 13 and 14 (FIG. 2), is designed as a pull/push rod in the illustrated embodiments.

When the medical instrument 1 is being assembled, the distal end of the medical instrument is joined to the tool tip 6, the distal-side pivoting members 11 and the actuating element 8 connected at the distal side to the tool tip 6 as well as the steering wires 12 mounted on the distal-side pivoting members 11 in a first step. In the subsequent assembly step, the steering wires 12 and the actuating element 8 have to be inserted into a hollow shaft tube 15 of the shaft 2 from the distal aspect.

In particular, when using many thin steering wires 12, it is very difficult to thread all steering wires 12 together through the hollow shaft tube 15 from the distal aspect in a crossing-free and sorted manner.

Figure 2:
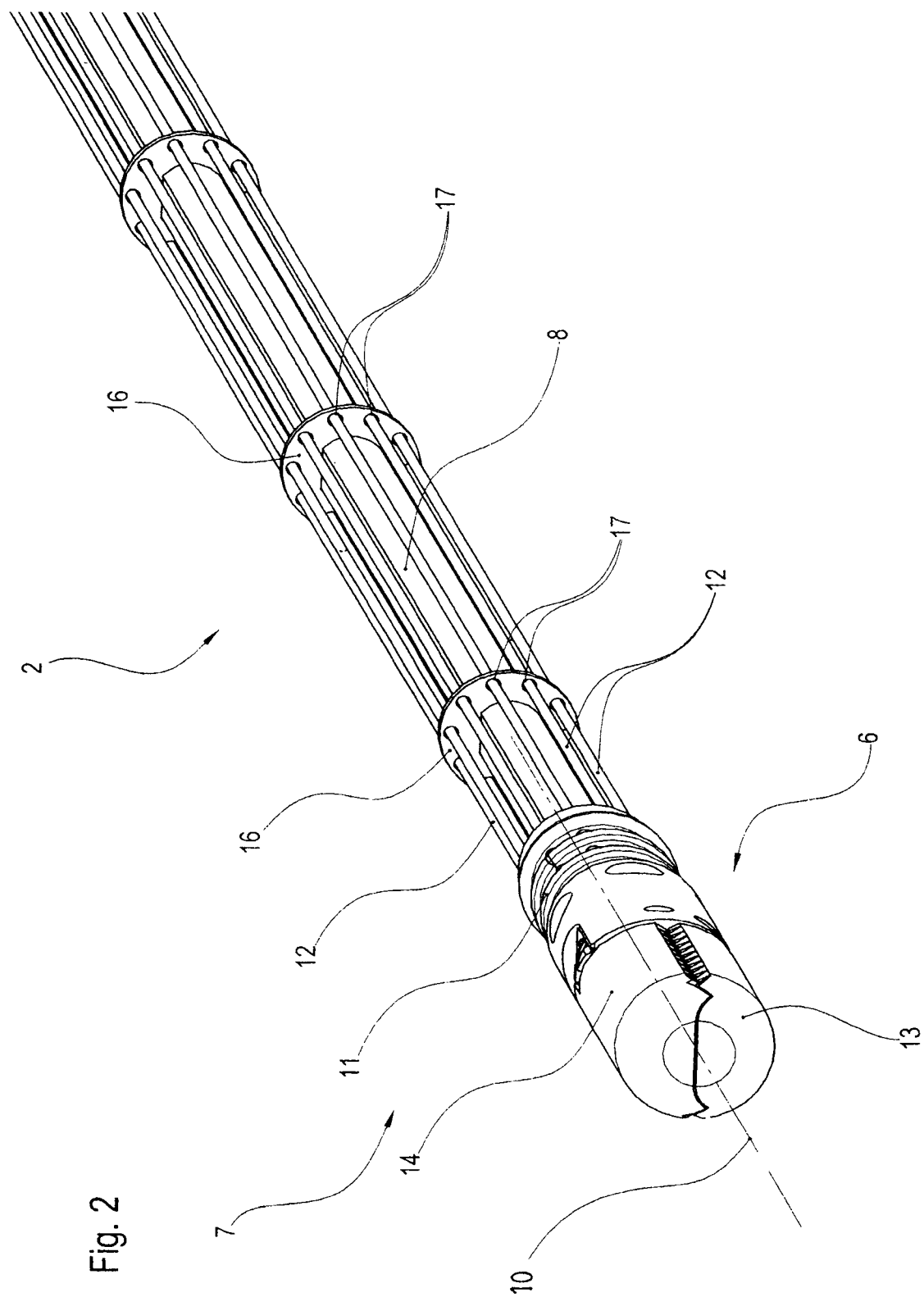
FIG. 2 shows an enlarged perspective view of area II according to FIG. 1 but with a medical instrument according to the invention without a shaft tube.
Figure 3:
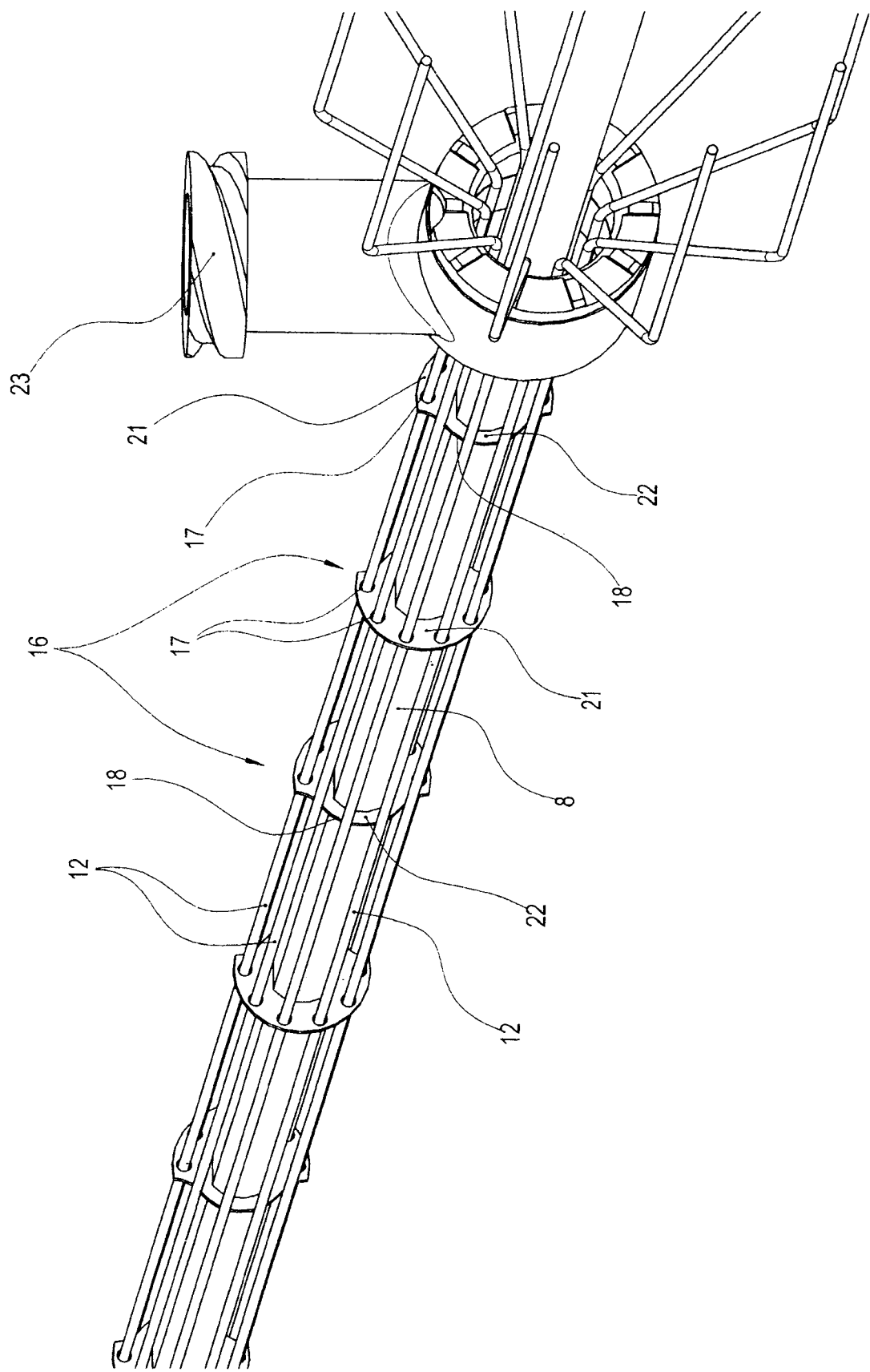
FIG. 3 shows a perspective view of the medical instrument, according to the invention, without a shaft tube according to FIG. 2 from the proximal perspective but representing an alternative embodiment of the guide devices.
Figure 4:
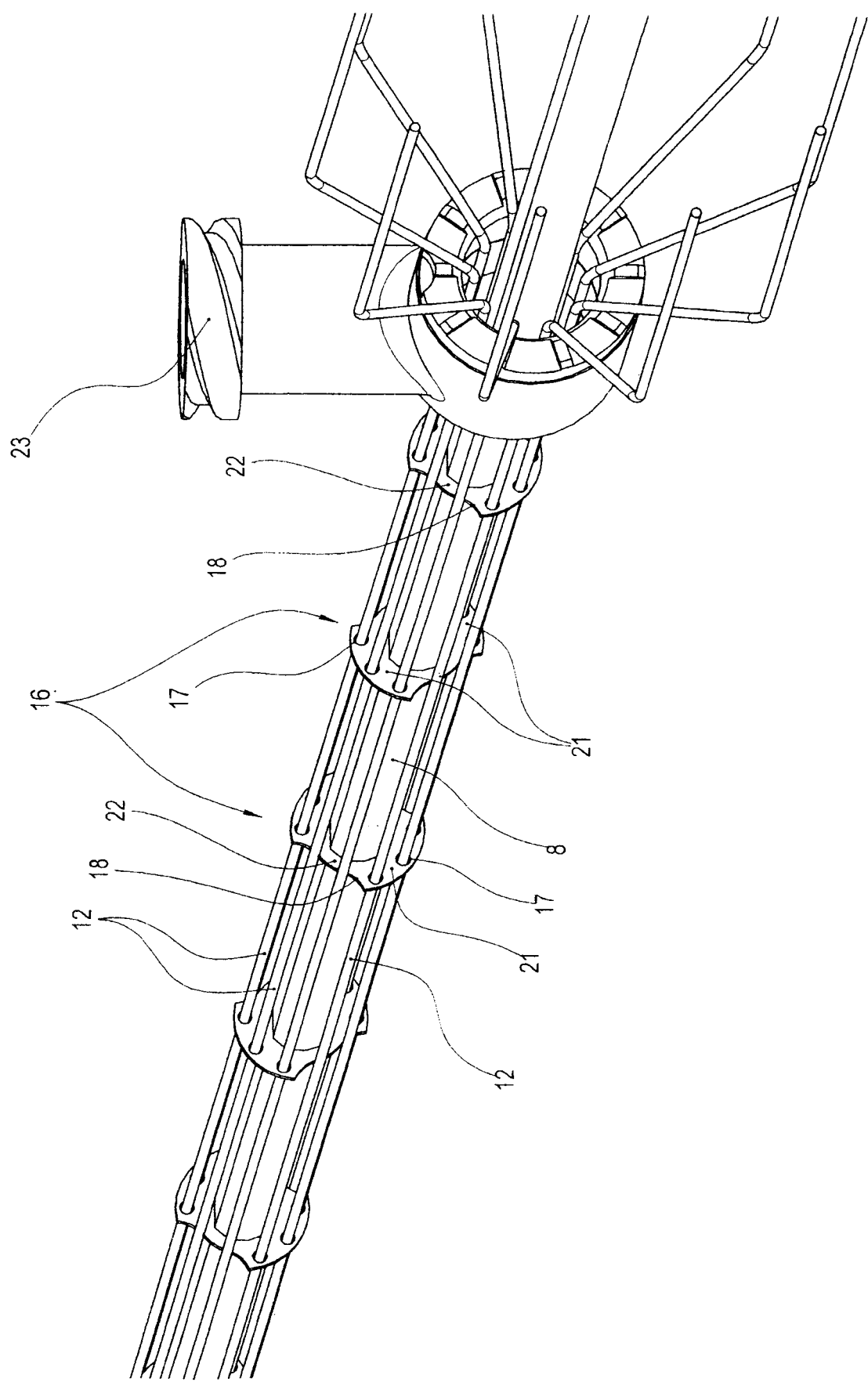
FIG. 4 shows a view according to FIG. 3 but presents a further alternative embodiment of the guide devices.

In order to ensure a crossing-free course of the steering wires 12 between the distal-side pivoting members 11 and the proximal-side drive 4a through the hollow shaft tube 15 as shown in the embodiments in FIGS. 2 to 4, at least one guide device 16 is arranged for the steering wires 12 connecting the pivoting members 11 to the drive 4a in the interior of the hollow shaft 2 between the distal-side pivoting members 11 and the proximal-side drive 4a with recesses 17 being formed for at least some of the steering wires 12 in the at least one guide device 16.

As can also be seen from FIGS. 2 to 4, a plurality of guide devices 16 are advantageously arranged one behind the other along the longitudinal axis 10 of the shaft 2 over the length of the shaft 2 in order to facilitate the threading into the hollow shaft tube 15.

In the embodiments shown, the guide devices 16 are designed as disk-shaped rings arranged coaxially on the actuating element 8 and transversely to the longitudinal axis 10 of the shaft 2.

Alternatively, it is also possible to arrange the guide device 16 on the inside of the ends of the hollow shaft tube 15 on both sides.

The arrangement of the guide devices 16 on the actuating element 8 has the advantage that the steering wires 12 can be placed into the recesses 17 in a very easy and quick manner, and, in addition, the actuating element 8 with the guide devices 16 and the steering wires 12 arranged in the recesses 17 of the guide devices 16 can be completely pre-assembled before these are then inserted into the hollow shaft tube 15 from the distal aspect.

In the embodiments shown in FIGS. 3 to 6 regarding the design of the guide devices 16, the guide devices 16 comprise at least one rinsing opening 18 in addition to the recesses 17 for the steering wires 12. The at least one rinsing opening 18 in the guide device 16 is intended to facilitate the flow around the guide devices 16 and thus the complete cleaning of the shaft tube 15 when the shaft tube 15 is being rinsed.

Figure 6:
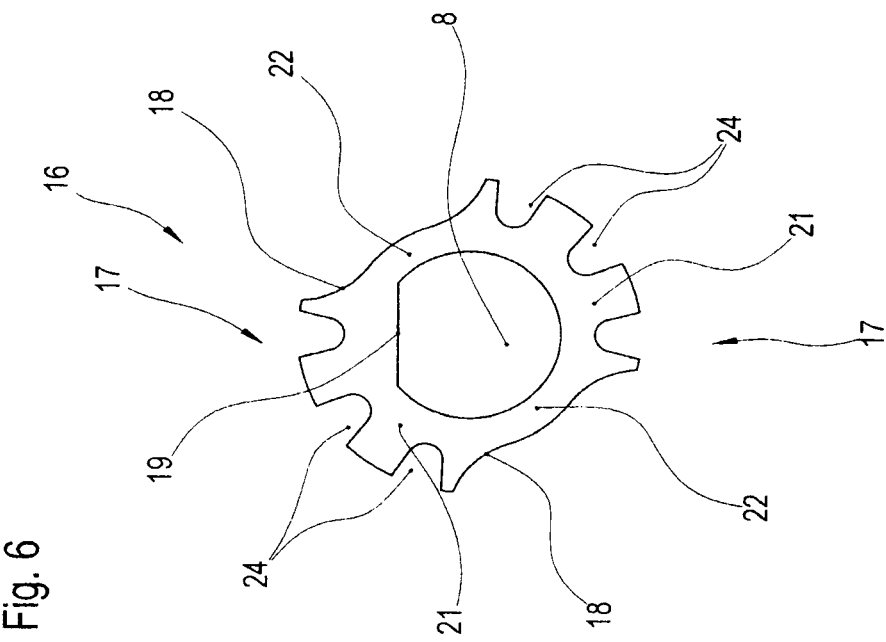
FIG. 6 shows a sectional view according to FIG. 5 but presents a further alternative embodiment of the guide devices.
Figure 5:
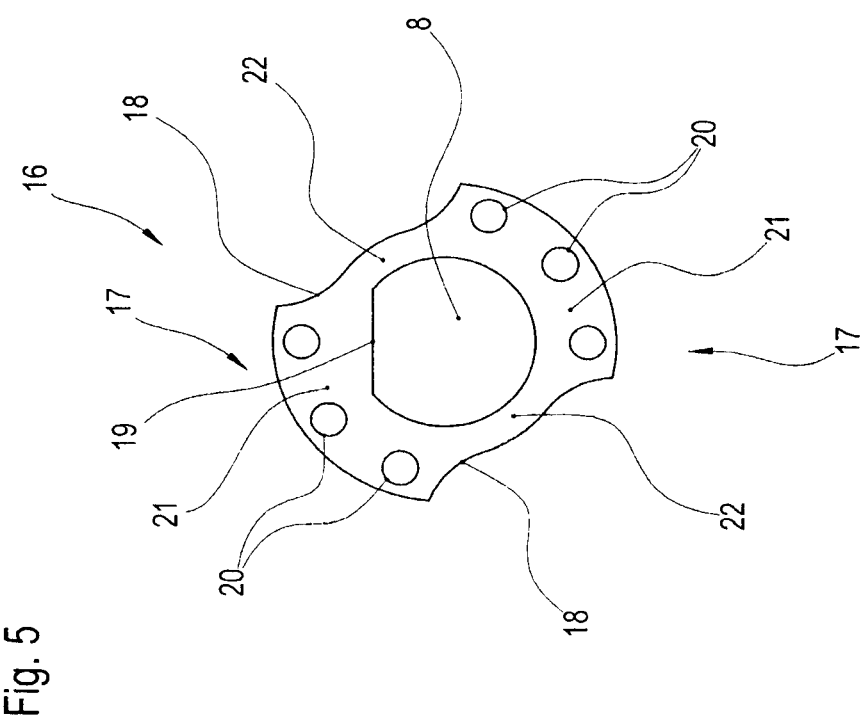
FIG. 5 shows an enlarged section along the line V-V of FIG. 4.

To ensure that the steering wires 12 arranged in the guide devices 16 cannot twist helically around the central actuating element 8, the guide devices 16 are advantageously mounted on the actuating element 8 in a manner that prevents them from rotating. As FIGS. 5 and 6 show, non-circular contact surfaces 19 corresponding to one another are formed on the guide device 16 and on the actuating element 8 in order to prevent any rotation.

As an alternative to forming the non-circular contact surfaces 19, it is, of course, also possible to fix the guide devices 16 on the actuating element 8 such that they cannot rotate, for example by welding or pressing.

In the embodiment of the guide device 16 shown in FIG. 2, the guide device 16 is designed as a complete disk-shaped ring in which a recess 17 designed as a through hole 20 is formed for each steering wire 12.

The embodiments shown in FIGS. 3 to 6 regarding the design of the guide devices 16 are characterized in that the disk-shaped rings have partial regions 21 with recesses 17 for the steering wires 12 and partial regions 22 for the rinsing opening 19.

If a plurality of guiding devices 16 is arranged one behind the other on the actuating element 8, as shown in FIGS. 3 and 4, it is sufficient for a secure and non-crossing guiding of the steering wires 12 if the single steering wire 12 is only guided in every second or third guiding device 16.

While in the embodiment shown in FIG. 3 each guide device 16 comprises a partial area 21 with recesses 17 for the steering wires 12 and a partial area 22 for the rinsing opening 18, there are two partial areas 21 with recesses 17 each for the steering wires 12 and two partial areas 22 each for the rinsing opening 18 in the embodiments shown in FIGS. 4 to 6.

As can be seen from FIGS. 3 and 4, two guide devices 16 arranged directly one behind the other in the direction of the longitudinal axis 10 of the shaft 2 are arranged so that the partial areas 21 provided with the recesses 17 for the steering wires 12 and the partial areas 22 provided with rinsing openings 18 are arranged such that they are offset from one another.

This offset arrangement of the partial regions 21 and 22 of the guide devices 16 relative to one another causes a rinsing liquid fed into the hollow shaft tube 15 via a proximal rinsing connection 23 to have to flow around the guide devices 16 in a meandering manner. The resulting turbulent flow represents an improvement in the cleaning effect compared to straight rinsing.

As an alternative to the embodiments shown, guide devices with more than two partial areas 21 and 22 can, of course, also be used.

Finally, FIG. 6 shows an alternative embodiment for the design of the recesses 17 for guiding the steering wires 12. In this embodiment, the recesses 17 are designed as radially inwardly extending slots 24 that are open toward the outside. This design enables each steering wire 12 to be inserted quickly and easily into the associated recess 17 of the guide device 16.

A medical instrument 1 configured as shown before is characterized in that each guide wire 12 is guided securely from the distal to the proximal side by means of the guide devices 16 so that there is never any risk of any mix-up or crossing over.

A positive side effect of this guided design is that the steering wires 12 do not rub against one another even during operation and do not influence one another in the steering behavior. Furthermore, the steering wires 12 guided between the distal pivoting members 11 and the proximal drive 4a by means of the guide devices 16 do not sag and can thus react more directly to tension.

The use of the guide devices 16 arranged in the interior of the shaft 2 for the steering wires 12 ensures a simple and crossing-free assembly of the steering wires 12.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

1 Medical instrument
2 Shaft
3 Proximal end (shaft)
4 Handle
4a Drive
5 Distal end (shaft)
6 Tool tip
7 Tool
8 Actuating element
9 Joint mechanism
10 Longitudinal axis
11 Pivoting member
12 Steering wire
13 Jaw part
14 Jaw part
15 Shaft tube
16 Guide device
17 Recess
18 Rinse opening
19 Contact surface
20 Through hole
21 Partial area
22 Partial area
23 Rinsing connection
24 Slot

We claim:

1. A medical instrument with a hollow shaft, a handle arranged at the proximal end of the shaft and a tool tip with a tool arranged at the distal end of the shaft, wherein the tool can be actuated via an actuating element mounted axially displaceable in the shaft, said actuating element being in an operative connection with the handle on the proximal side and the tool tip being pivotable relative to the longitudinal axis of the shaft via a joint mechanism, the joint mechanism having distal-side pivoting members arranged at the distal end of the shaft, which are connected with a proximal-side drive via steering wires running in the longitudinal direction of the shaft in such a way that a movement of the proximal-side drive causes a corresponding relative movement of the distal-side pivoting members and thus a swiveling of the tool tip, wherein inside the hollow shaft between the distal-side pivoting members and the proximal-side drive at least one guide device is arranged for the steering wires connecting the distal-side pivoting members to the proximal-side drive, wherein recesses are formed in the at least one guide device for at least some of the steering wires, characterized in that: the at least one guide device is arranged coaxially and directly on the actuating element, and the at least one guide device is mounted on the actuating element such that contacting surfaces of the at least one guide device and the actuating element are arranged in such a manner that the at least one guide device cannot rotate so as to prevent a helically twisting of the steering wires around the actuating element.

2. The medical instrument according to claim 1, characterized in that one or more non-circular contact surfaces corresponding to one another are formed on the at least one guide device and on the actuating element to prevent rotation.

3. The medical instrument according to claim 1, characterized in that the actuating element is designed as a pull/push rod.

4. The medical instrument according to claim 1, characterized in that the at least one guide device comprises at least one rinsing opening in addition to the recesses for the steering wires.

5. The medical instrument according to claim 1, characterized in that the at least one guide device is designed as a disk-shaped ring that is arranged transversely to the longitudinal axis of the shaft.

6. The medical instrument according to claim 5, characterized in that the at least one guide device designed as a disk-shaped ring comprises at least one partial area with the recesses for the steering wires and at least one partial area with a rinsing opening.

7. The medical instrument according to claim 6, characterized in that the at least one guide device designed as a disk-shaped ring comprises two partial areas with the recesses for the steering wires and two partial areas with rinsing openings, with the respective partial areas being arranged offset to one another.

8. The medical instrument according to claim 6 with the at least one guide device comprises at least two guide devices arranged on the actuating element and designed as a disk-shaped ring, characterized in that in each case two guide devices arranged one behind the other in the direction of the longitudinal axis of the shaft are arranged with respect to one another such that the partial areas with the recesses for the steering wires and the partial areas with rinsing openings are offset with respect to one another.

9. The medical instrument according to claim 1, characterized in that the at least one guide device comprises at least two guide devices which are arranged on the actuating element at a distance from one another.

10. The medical instrument according to claim 1, characterized in that the recesses formed for the steering wires in the at least one guide device are designed as through holes.

11. The medical instrument according to claim 1, characterized in that the recesses formed in the at least one guide device for the steering wires are designed as radial inwardly open slots that are open to the outside.

* * * * *